United States Patent
Pedicini

(10) Patent No.: US 10,342,591 B2
(45) Date of Patent: Jul. 9, 2019

(54) ELECTRIC MOTOR DRIVEN TOOL FOR ORTHOPEDIC IMPACTING

(71) Applicant: DePuy Synthes Products, Inc., Raynham, MA (US)

(72) Inventor: Christopher Pedicini, Nashville, TN (US)

(73) Assignee: DePuy Synthes Products, Inc., Raynham, MA (US)

( * ) Notice: Subject to any disclaimer, the term of this patent is extended or adjusted under 35 U.S.C. 154(b) by 571 days.

(21) Appl. No.: 14/992,781

(22) Filed: Jan. 11, 2016

(65) Prior Publication Data

US 2016/0199199 A1 Jul. 14, 2016

Related U.S. Application Data

(60) Provisional application No. 62/101,416, filed on Jan. 9, 2015.

(51) Int. Cl.
*A61F 2/46* (2006.01)
*A61B 17/92* (2006.01)
(Continued)

(52) U.S. Cl.
CPC ............ *A61B 17/92* (2013.01); *A61F 2/4603* (2013.01); *B25D 11/068* (2013.01); *B25D 11/125* (2013.01); *A61F 2002/469* (2013.01); *A61F 2002/4627* (2013.01); *A61F 2002/4681* (2013.01)

(58) Field of Classification Search
CPC ........... A61F 2/46; A61F 2/4603; A61B 17/92
See application file for complete search history.

(56) References Cited

U.S. PATENT DOCUMENTS 4,431,062 A * 2/1984 Wanner ................ B25D 11/08
173/104
5,057,112 A 10/1991 Sherman et al.
(Continued)

FOREIGN PATENT DOCUMENTS

EP 0 617 926 A2 10/1994
EP 0 617 926 A3 10/1994
(Continued)

OTHER PUBLICATIONS

International Search Report and Written Opinion dated Jun. 9, 2016 in PCT/US2016/012917 filed Jan. 11, 2016.

*Primary Examiner* — Christopher J Beccia

(57) ABSTRACT

An orthopedic impacting tool including a motor, an energy storage chamber, a striker, and an anvil. The motor stores energy in the energy storage chamber and then releases it, causing the striker to apply a controlled force on an adapter to create a precise impact for use in a surgical setting. The tool may further comprise a combination anvil and adapter. Alternatively, the tool may comprise a gas spring assembly system for generating an impact force. The tool further allows forward or backward impacting for expanding the size or volume of the opening or for facilitating removal of a broach, implant, or other surgical implement from the opening. An energy adjustment control of the tool allows a surgeon to increase or decrease the impact energy. A light source and hand grips improve ease of operation of the tool.

19 Claims, 15 Drawing Sheets

(51) Int. Cl.
*B25D 11/06* (2006.01)
*B25D 11/12* (2006.01)

(56) References Cited

U.S. PATENT DOCUMENTS

| | | |
|---|---|---|
| 6,264,660 B1 | 7/2001 | Schmidt et al. |
| 6,413,230 B1 | 7/2002 | Haupt et al. |
| 6,520,266 B2 * | 2/2003 | Bongers-Ambrosius .................... B25D 11/12 173/115 |
| 6,938,705 B2 | 9/2005 | Kikuchi |
| 7,189,241 B2 | 3/2007 | Yoon et al. |
| 8,465,491 B2 | 6/2013 | Yedlicka et al. |
| 8,926,625 B2 | 1/2015 | Lebet |
| 8,936,603 B2 | 1/2015 | Mani et al. |
| 8,936,604 B2 | 1/2015 | Mani et al. |
| 8,968,326 B2 | 3/2015 | Mani et al. |
| 2005/0065529 A1 * | 3/2005 | Liu ...................... A61B 17/025 606/79 |
| 2008/0215056 A1 | 9/2008 | Miller et al. |
| 2013/0161050 A1 | 6/2013 | Pedicini |
| 2013/0261681 A1 | 10/2013 | Bittenson |
| 2015/0127013 A1 | 5/2015 | Mani et al. |
| 2015/0182233 A1 | 7/2015 | Van Wyk et al. |
| 2015/0289886 A1 | 10/2015 | Kfir |

FOREIGN PATENT DOCUMENTS

| | | |
|---|---|---|
| EP | 0 617 926 B1 | 8/1998 |
| GB | 2 115 886 A | 9/1983 |

* cited by examiner

ELECTRIC MOTOR DRIVEN TOOL FOR ORTHOPEDIC IMPACTING

CROSS-REFERENCE TO RELATED APPLICATIONS

The present application claims the benefit of 35 USC § 119 to U.S. Provisional Patent Application No. 62/101,416, filed on Jan. 9, 2015, the entire disclosure of which is incorporated by reference.

FIELD OF THE DISCLOSURE

The present disclosure relates to electric tools for impacting in surgical applications such as orthopedic procedures, and, more particularly, to an electric motor driven tool for surgical impacting that is capable of providing controlled impacts to a broach or other end effector.

BACKGROUND

In the field of orthopedics, prosthetic devices, such as artificial joints, are often implanted or seated in a patient's bone cavity. The cavity is typically formed during surgery before the prosthesis is seated or implanted, for example, a physician may remove and or compact existing bone to form the cavity. A prosthesis usually includes a stem or other protrusion that is inserted into the cavity.

To create the cavity, a physician may use a broach conforming to the shape of the stem of the prosthesis. Solutions known in the art include providing a handle with the broach for manual hammering by the physician during surgery to impel the broach into the implant area. Unfortunately, this approach is imprecise, leading to unnecessary mechanical stress on the bone and highly unpredictable depending upon the skill of a particular physician. Historically, this brute force approach will in many cases result in inaccuracies in the location and configuration of the cavity. Additionally, the surgeon is required to expend an unusual amount of physical force and energy to hammer the broach and to manipulate the bones and prosthesis. Most importantly, this approach carries with it the risk that the physician will cause unnecessary further trauma to the surgical area and damage otherwise healthy tissue, bone structure and the like.

Another technique for creating the prosthetic cavity is to drive the broach pneumatically, that is, by compressed air. This approach is disadvantageous in that it prevents portability of an impacting tool, for instance, because of the presence of a tethering air-line, air being exhausted from a tool into the sterile operating field and fatigue of the physician operating the tool. This approach, as exemplified in U.S. Pat. No. 5,057,112, does not allow for precise control of the impact force or frequency and instead functions very much like a jackhammer when actuated. Again, this lack of any measure of precise control makes accurate broaching of the cavity more difficult, and leads to unnecessary patient complications and trauma.

A third technique relies on computer-controlled robotic arms for creating the cavity. While this approach overcomes the fatiguing and accuracy issues, it suffers from having a very high capital cost and additionally removes the tactile feedback that a surgeon can get from a manual approach.

A fourth technique relies on the author's own, previous work to use a linear compressor to compress air on a single stroke basis and then, after a sufficient pressure is created, to release the air through a valve and onto a striker. This then forces the striker to travel down a guide tube and impact an anvil, which holds the broach and or other surgical tool. This invention works quite well, but, in the process of testing it, does not allow for a simple method to reverse the broach should it become stuck in the soft tissue. Further, the pressure of the air results in large forces in the gear train and linear motion converter components, which large forces lead to premature wear on components.

Consequently, there exists a need for an impacting tool that overcomes the various disadvantages of existing systems and previous proprietary solutions of the inventor

SUMMARY

In view of the foregoing disadvantages, an electric motor-driven orthopedic impacting tool is provided for orthopedic impacting in hips, knees, shoulders and the like. The tool is capable of holding a broach, chisel, or other end effector and gently tapping the broach, chisel or other end effector into the cavity with controlled percussive impacts, resulting in a better fit for the prosthesis or the implant. Further, the control afforded by such an electrically manipulated broach, chisel, or other end effector allows adjustment of the impact settings according to a particular bone type or other profile of a patient. The tool additionally enables proper seating or removal of the prosthesis or the implant into or out of an implant cavity and advantageously augments the existing surgeon's skill in guiding the instrument.

In an exemplary embodiment, an electric motor-driven orthopedic impacting tool comprises a local power source (such as a battery or fuel cell), a motor, a controller, a housing, a module for converting the rotary motion of the motor to a linear motion (hereafter referred to as a linear motion converter), at least one reducing gear, a striker, a detent and an energy storage mechanism, which energy storage mechanism can include either compressed air or a vacuum. The tool may further include an LED, a handle portion with at least one handgrip for the comfortable gripping of the tool, an adapter configured to accept a surgical tool, a battery and at least one sensor. At least some of the various components are preferably contained within the housing. The tool is capable of applying cyclic impact forces on a broach, chisel, or other end effector, or an implant and of finely tuning an impact force to a plurality of levels. As no connections to the device are required, the device is portable.

In another embodiment, the orthopedic impacting tool may comprise a gas spring assembly system for generating an impact force applied to a broach, chisel, or other end effector. The gas spring assembly system is actuatable by a motor and gearbox in combination with a cam, which releases a gas spring piston that, in turn, accelerates a launching mass for generating the impact force. As an example, after a sufficient displacement of the gas spring piston, in which stored potential energy of the gas spring is increased, the gas spring piston is released from the cam. Upon release of the gas spring piston, the launched mass is accelerated in the forward direction with the gas spring piston until it comes into operative contact with the point of impact, the anvil or another impact surface. In an embodiment, the launched mass separates from the gas spring piston prior to its point of impact. There are at least two different impacting surfaces for the launched mass, a forward impact surface and a different surface for rearward impact. The ratio of the gas spring piston mass to the total moving mass, i.e., the gas spring piston in combination with the launched mass, is less than 50%, which facilitates a more efficient transfer of energy to the launched mass for imparting an effective impact. Further, the compression ratio of the gas spring is less than about 50%, which reduces thermal losses from the heat of compression. After the launched mass impacts the impact surface or point of contact, the cam re-cocks the gas spring piston for the next cycle, if a trigger is maintained.

In a further embodiment, the handle may be repositionable or foldable back to the tool to present an inline tool wherein the surgeon pushes or pulls on the tool co-linearly with the direction of the broach. This has the advantage of limiting the amount of torque the surgeon may put on the tool while it is in operation. In a further refinement of the hand grip, there may be an additional hand grip for guiding the surgical instrument and providing increased stability during the impacting operation.

In a further embodiment, the broach, chisel or other end effector can be rotated to a number of positions while still maintaining axial alignment. This facilitates the use of the broach for various anatomical presentations during surgery.

In a further embodiment, the energy storage mechanism comprises a chamber, which is under at least a partial vacuum during a portion of an impact cycle.

In a further embodiment the linear motion converter uses one of a slider crank, linkage mechanism, cam, screw, rack and pinion, friction drive or belt and pulley.

In an embodiment, the linear motion converter and rotary motor may be replaced by a linear motor, solenoid or voice coil motor.

In a further embodiment, the tool further comprises a control element, which includes an energy adjustment element, and which energy adjustment element may control the impact force of the tool and reduce or avoid damage caused by uncontrolled impacts. The energy may be regulated electronically or mechanically. Furthermore, the energy adjustment element may be analog or have fixed settings. This control element allows for the precise control of the broach machining operation.

In an embodiment, an anvil of the tool includes at least one of two points of impact and a guide that constrains the striker to move in a substantially axial direction. In operation, the movement of the striker along the guide continues in the forward direction. A reversing mechanism can be used to change the point of impact of the striker and the resulting force on the surgical tool. Use of such a reversing mechanism results in either a forward or a rearward force being exerted on the anvil and/or the broach or other surgical attachment. As used in this context, "forward direction" connotes movement of the striker toward a broach, chisel or patient, and "rearward direction" connotes movement of the striker away from the broach, chisel or patient. The selectivity of either bidirectional or unidirectional impacting provides flexibility to a surgeon in either cutting or compressing material within the implant cavity in that the choice of material removal or material compaction is often a critical decision in a surgical procedure. Furthermore, it was discovered in the use of the author's own, previous work that the tool would often get stuck during the procedure and that the method of reversal in that tool was insufficient to dislodge the surgical implement. The present embodiments disclosed herein overcome this drawback. In an embodiment the impact points to communicate either a forward or rearward force are at least two separate and distinct points.

In an embodiment the anvil and the adapter comprise a single element, or one may be integral to the other.

In an embodiment the tool is further capable of regulating the frequency of the striker's impacting movement. By regulating the frequency of the striker, the tool may, for example, impart a greater total time-weighted percussive impact, while maintaining the same impact magnitude. This allows for the surgeon to control the cutting speed of the broach or chisel. For example, the surgeon may choose cutting at a faster rate (higher frequency impacting) during the bulk of the broach or chisel movement and then slow the cutting rate as the broach or chisel approaches a desired depth. In typical impactors, as shown in U.S. Pat. No. 6,938,705, as used in demolition work, varying the speed varies the impact force, making it impossible to maintain constant (defined as +/−20%) impact energy in variable speed operation.

In an embodiment the direction of impacting is controlled by the biasing force placed by a user on the tool. For example, biasing the tool in the forward direction gives forward impacting and biasing the tool in the rearward direction gives rear impacting.

In an embodiment the tool may have a lighting element to illuminate a work area and accurately position the broach, chisel, or other end effector on a desired location on the prosthesis or the implant.

In an embodiment the tool may also include a feedback system that warns the user when a bending or off-line orientation beyond a certain magnitude is detected at a broach, chisel, or other end effector or implant interface.

In an embodiment the tool may also include a detent that retains the striker and which may be activated by a mechanical or electrical controller such that the energy per impact from the tool to the surgical end effector is increased. In an embodiment, the characteristics of this detent are such that within 30% of striker movement, the retention force exerted by the detent on the striker is reduced by about 50%.

These together with other aspects of the present disclosure, along with the various features of novelty that characterize the present disclosure, are pointed out with particularity in the claims annexed hereto and form a part of the present disclosure. For a better understanding of the present disclosure, its operating advantages, and the specific non-limiting objects attained by its uses, reference should be made to the accompanying drawings and detailed description in which there are illustrated and described exemplary embodiments of the present disclosure.

DESCRIPTION OF THE SEVERAL VIEWS OF THE DRAWINGS

The advantages and features of the present invention will become better understood with reference to the following detailed description and claims taken in conjunction with the accompanying drawings, wherein like elements are identified with like symbols, and in which:

DETAILED DESCRIPTION OF THE DISCLOSURE

Figure 1:
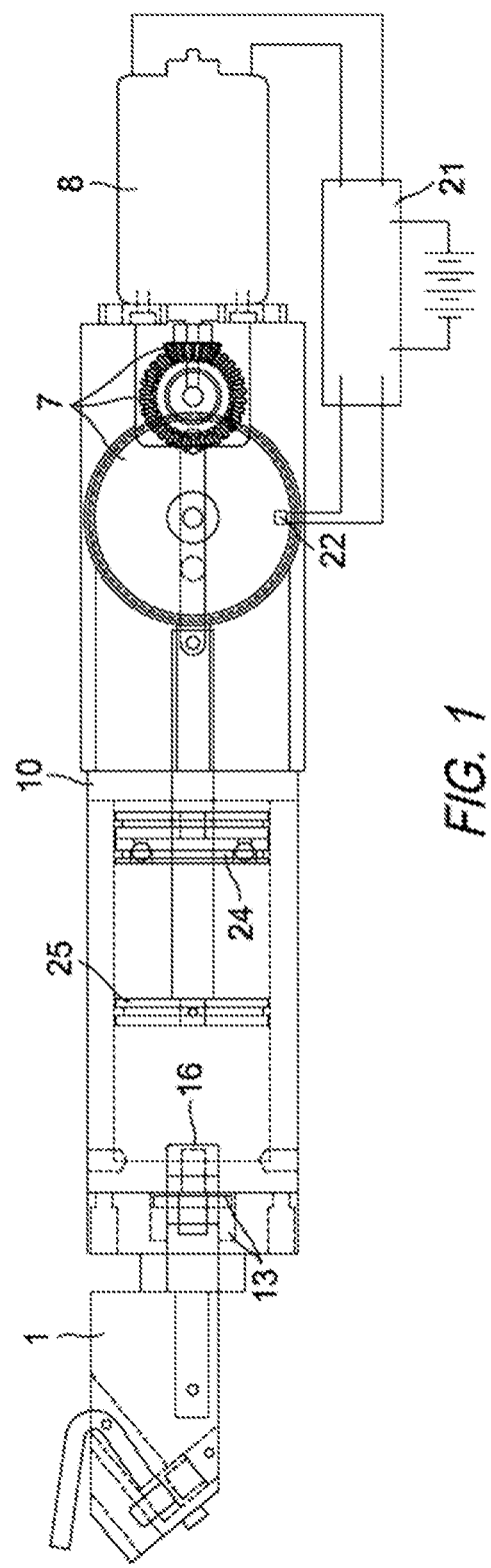
FIG. 1 shows a perspective view of an orthopedic impacting tool in accordance with an exemplary embodiment of the present disclosure.

The preferred embodiments described herein detail for illustrative purposes are subject to many variations. It is understood that various omissions and substitutions of equivalents are contemplated as circumstances may suggest or render expedient, but are intended to cover the application or implementation without departing from the spirit or scope of the present disclosure.

The present disclosure provides an electric motor-driven orthopedic impacting tool with controlled percussive impacts. The tool includes the capability to perform single and multiple impacts as well as impacting of variable and varying directions, forces and frequencies. In an embodiment the impact force is adjustable. In another embodiment a detent may be provided, which detent facilitates the generation of a higher energy impact. In yet another embodiment the impact is transferred to a broach, chisel, or other end effector connected to the tool.

The tool may further include a housing. The housing may securely cover and hold at least one component of the tool and is formed of a material suitable for surgical applications. In an embodiment, the housing contains a motor, at least one reducing gear, a linear motion converter, a gas chamber, a striker, a force adjuster, a control circuit or module, an anvil, a forward impact surface and a different surface for rearward impact.

The tool further may include a handle portion with an optional hand grip for comfortable and secure holding of the tool while in use, and an adapter, a battery, a positional sensor, a directional sensor, and a torsional sensor. The tool may further comprise a lighting element such as an LED to provide light in the work area in which a surgeon employs the tool. The anvil may be coupled to a broach, chisel or other end effector known in the art through the use of an interfacing adapter, which adapter may have a quick connect mechanism to facilitate rapid change of different broaching sizes. The anvil may further include a locking rotational feature to allow the broach to be presented to and configured at different anatomical configurations without changing the orientation of the tool in the surgeon's hands.

Referring now generally to FIGS. 1 through 5, in an exemplary embodiment, the linear motion converter 12 comprises a slider crank mechanism. The slider crank is operatively coupled, directly or indirectly, to the motor 8 and reducing gears 7. The tool further comprises a vacuum chamber 23 that accepts a piston 24 which may be actuated by the linear motion converter 12. It will be apparent that the piston 24 may be actuated in more than one direction. The vacuum is created in the vacuum chamber 23 by the movement of piston 24 away from striker 25. The vacuum created in the vacuum chamber 23 is defined as a pressure of less than about 9 psia for at least a portion of the operational cycle.

Figure 2:
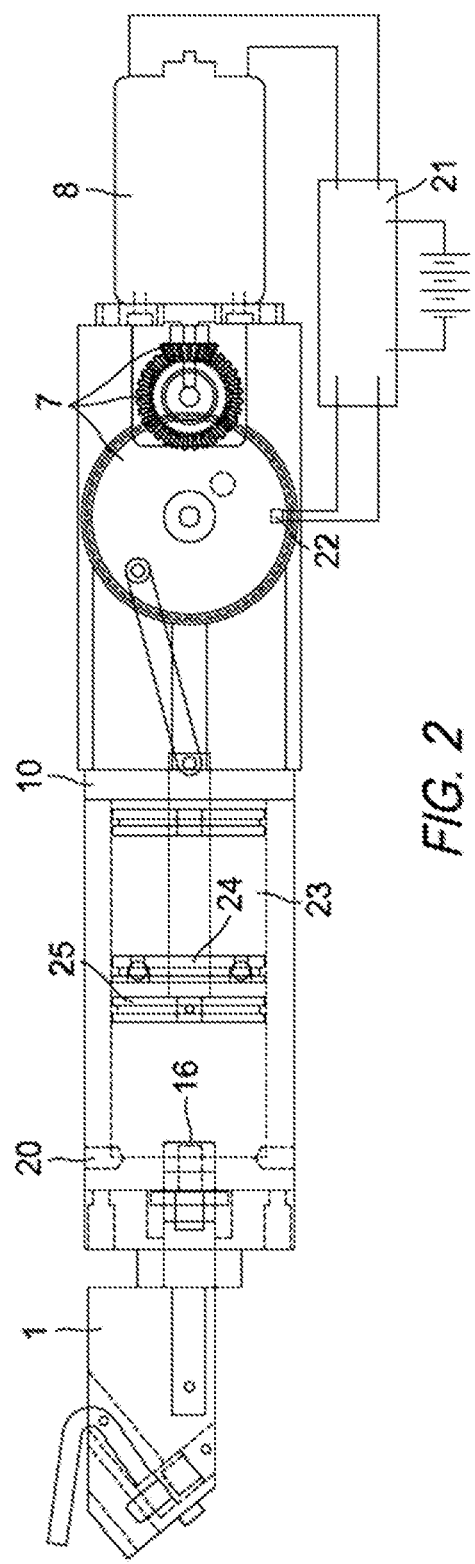
FIG. 2 shows an exemplary position of a piston of the tool of FIG. 1 during vacuum operation.

In an embodiment, the motor 8 causes the linear motion converter 12 to move, which pulls a vacuum on the face of the striker 25 and creates at least a partial vacuum in the vacuum chamber 23, as is shown more particularly in FIG. 2. The piston 24 continues to move increasing the size of the vacuum chamber 23 until it hits a forward portion of the striker 25 (i.e., a portion of the strike that is proximate to the end effector or patient), which dislodges the striker 25 from its detent 10 (for embodiments employing a detent) and allows it to rapidly accelerate towards the end of the tool that is proximate to the end effector or patient. In an embodiment, the detent may be mechanical, electrical, or a combination thereof, with the preferred detent shown in the figures as a magnet or electromagnet. A characteristic of the detent 10 is that once the detent 10 is released or overcome, the retention force of the detent 10 on the striker 25 reduces by at least about 50% within the first 30% movement of the striker 25. The impact of the striker 25 on the anvil 14 communicates a force to the adapter 1 and the broach, chisel or other orthopedic instrument.

In an exemplary embodiment, the direction of the force on the anvil is controlled by the user's (such as a surgeon) manual force on the tool and a stroke limiter 13. It has been determined by the inventor that his previous designs may occasionally seize in a cavity and the impact of the striker in the aforementioned paragraph may be insufficient to dislodge the tool. In this present embodiment, when the tool is being pulled away from the cavity, the striker 25 will not impact the anvil 14, but will impact an alternate surface and thereby communicate a rearward force on the anvil 14. This impact surface is shown in an exemplary embodiment as actuation pin 27. Actuation pin 27 communicates a force to lever arm 17, which communicates a rearward force on the anvil 14, and specifically on the anvil retract impact surface 26. This embodiment has the unexpected benefit of readily solving the aforementioned seizure problem, while retaining all the benefits of the existing tool in terms of precision-controlled impacting. Thus, a further advantage of this tool was discovered as it can be seen that the surgeon can control the direction of the impacting by a bias that he or she may place on the tool and, in so doing, can reduce the likelihood of the broach, chisel or other end effector from getting stuck in a patient or surgical cavity.

In a further embodiment, an electromagnet may be incorporated as the detent 10 and released at an appropriate point in the operation cycle to allow the striker 25 to impact the anvil 14. Once the striker 25 has been released from the detent 10, the air pressure on the rearward side of the striker 25, propels it forward to impact the anvil 14 or other strike surface. The resultant force may be communicated through an end of the anvil 14 that is proximate to the anvil forward impact surface 16 and, optionally, through the adapter 1 to which a broach, chisel, or other end effector for seating or removing an implant or prosthesis may be attached.

The striker guide 11 may also have striker guide vent holes 20, which allow the air in front of the striker 25 to escape, thus increasing the impact force of the striker 25 on the anvil 14. The striker guide vent holes 20 may vent within the cavity of the tool body, thus creating a self-contained air cycle preventing air from escaping from the tool and allowing for better sealing of the tool. The inventor has determined that the position and the size of the striker guide vent holes 20 can be varied to regulate the impact force. Further, the inventor determined that adding the striker guide vent holes 20 increases the impact force of the striker 25 on the anvil 14.

In an embodiment, as the piston 24 continues through its stroke it moves towards the rear direction. This movement brings the piston 24 in contact with rear striker face 28 of striker 25 and moves it towards the rear of the tool. This allows the detent 10 to lock or retain the striker 25 in position for the next impact. The piston 24 completes its rearward stroke and preferably activates a sensor 22 that signals the motor 8 to stop such that the piston 24 rests at or near bottom dead center of the vacuum chamber 23. The vacuum chamber 23 preferably has a relief or check valve 9 or other small opening, which, in an embodiment, is part of the piston 24. The valve 9 may also be located at other points in the vacuum chamber 23 and allows for any air which may have accumulated in the vacuum chamber 23 to be purged out of the vacuum chamber 23 during each cycle. In a further embodiment this valve effect could be accomplished with a cup seal instead of an O-ring seal. This ensures that approximately atmospheric pressure is present in the vacuum chamber 23 at a starting point in the operational cycle, thus ensuring that each impact utilizes the same amount of energy, as is important in orthopedic impacting for at least the reason that it assures of a substantially consistent force and impact rate in multi-impact situations. Thus, in one complete cycle, a forward or a rearward impacting force may be applied on the broach, chisel, or other end effector, or on the implant or prosthesis.

Figure 15:
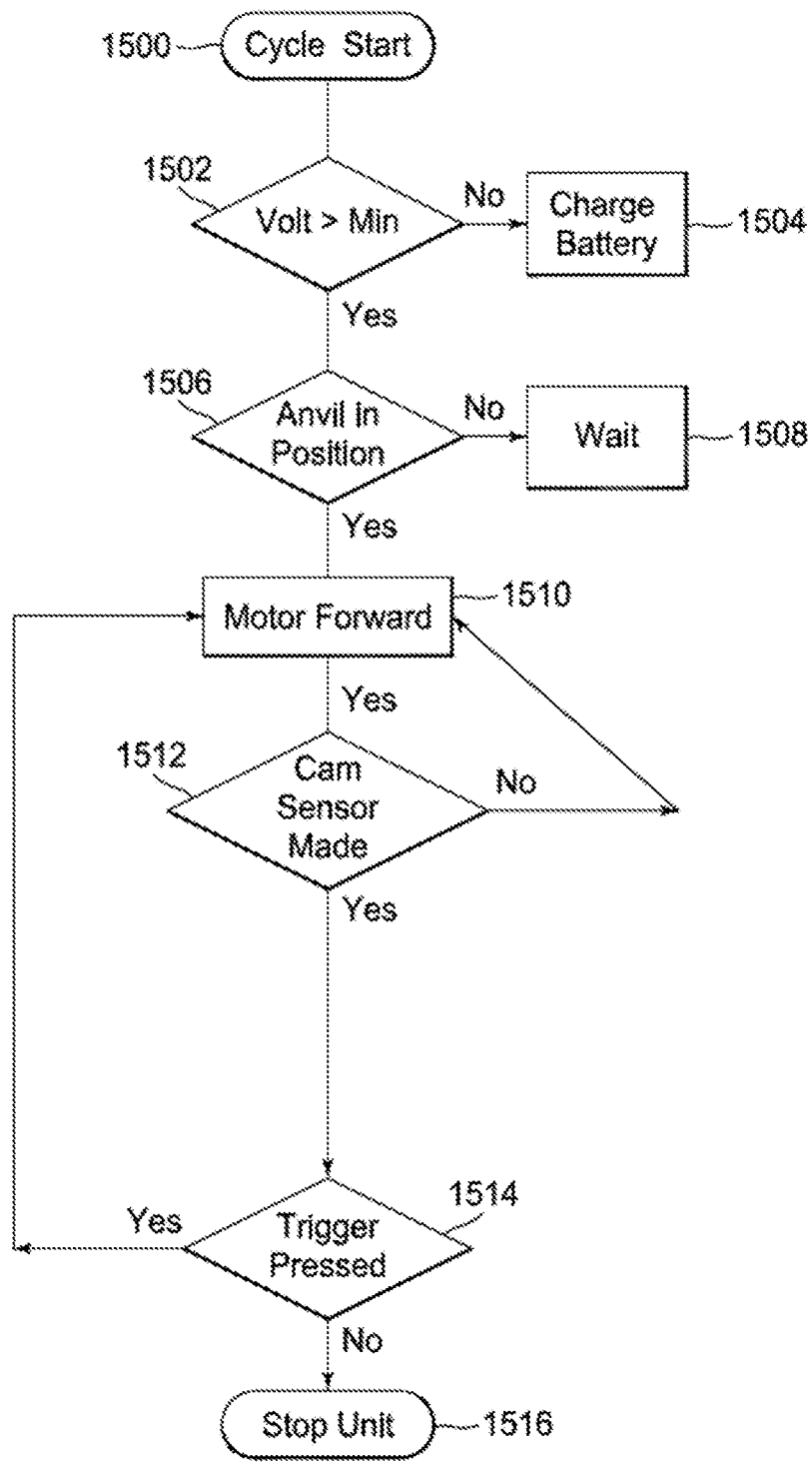
FIG. 15 is an exemplary flow chart illustrating a cyclic operation of an orthopedic impacting tool in accordance with an exemplary embodiment of the present disclosure.

FIG. 15 is an exemplary flow chart illustrating a cyclic operation of an orthopedic impacting tool according to an exemplary embodiment of the present disclosure. At the start of the cycle 1500, it is first determined in step 1502 whether the orthopedic impacting tool is charged and ready for use. If a voltage of a local power source, such as a battery, is less than a threshold minimum, then the battery is set to charge in step 1504. If the voltage of the battery is greater than the threshold minimum, then it is next determined in step 1506 whether an anvil and/or broach or other surgical attachment is correctly positioned relative to a cavity of the patient's bone. If the anvil and/or the broach or other surgical attachment is correctly positioned, the operation moves on to step 1510; otherwise, the system waits until the position is corrected in step 1508. In step 1510, it is determined whether an electric motor and gearbox combination is rotating. Once the motor starts to rotate, it is next determined in step 1512 whether a cam sensor has been activated. If the sensor has been activated, then a trigger is pressed in step 1514, which results in a cam to "cock" a gas spring piston and ultimately generate an impact force. If the cam sensor has not been activated, then the process returns to step 1510 to allow the motor to continue rotating until the cam sensor has been activated. Next, if a trigger is maintained in step 1514, then the operation cycles back to step 1510 where the motor continues to rotate, causing the cam to "re-cock" the gas spring piston for the next cycle; otherwise, the operation of the orthopedic impacting tool ceases at step 1516.

A controller 21 preferably operates with firmware implementing the cyclic operation described in FIG. 15, which results in the orthopedic impacting tool being able to generate a repeatable, controllable impacting force. The controller 21 can include, for example, intelligent hardware devices, e.g., any data processor, microcontroller or FPGA device, such as those made by Intel® Corporation (Santa Clara, Calfi.) or AMD® (Sunnyvale, Calif.). Other controller types could also be utilized, as recognized by those skilled in the art.

Figure 3:
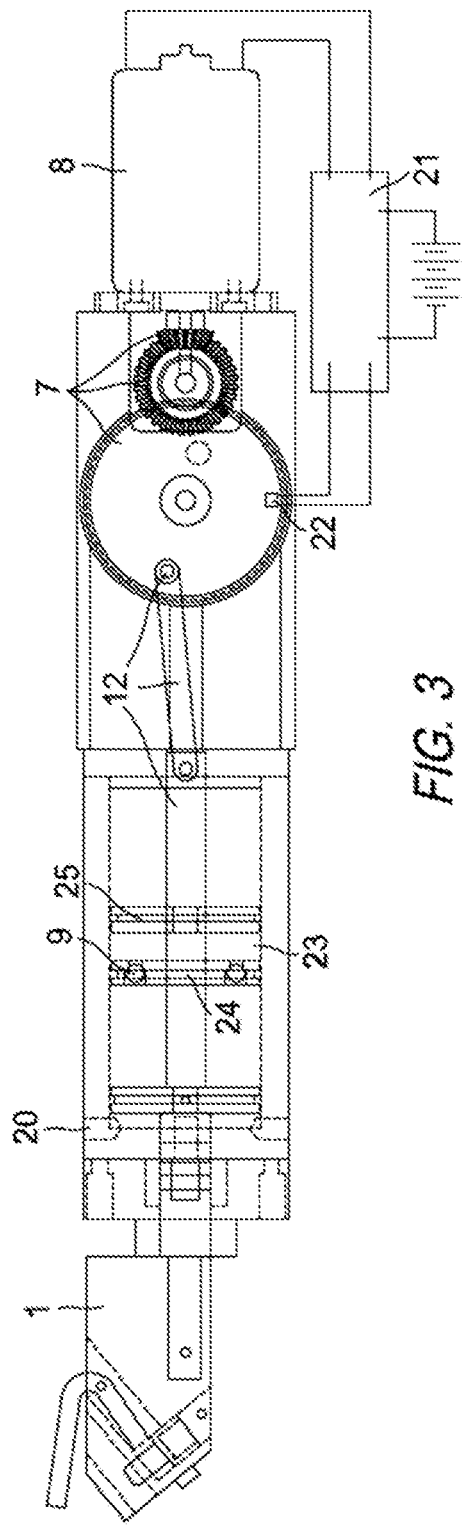
FIG. 3 shows a striker of the tool of FIG. 1 moving towards impacting the anvil in a forward direction.
Figure 4:
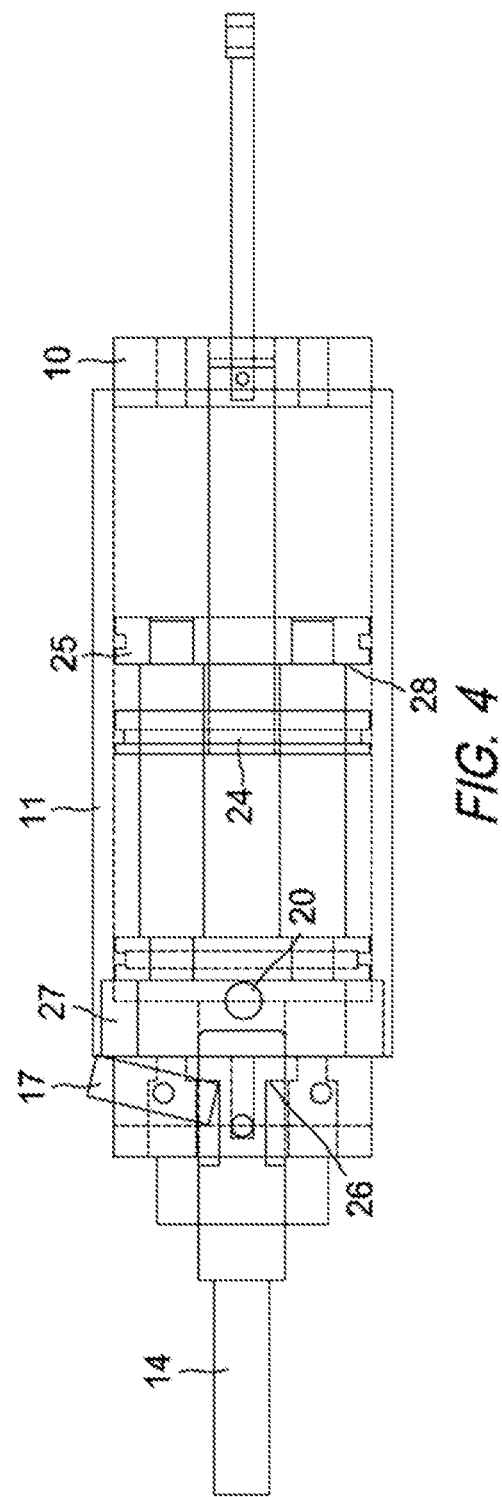
FIG. 4 shows the striker of the tool of FIG. 1 moving such that the anvil will be impacted in a reverse direction.
Figure 5:
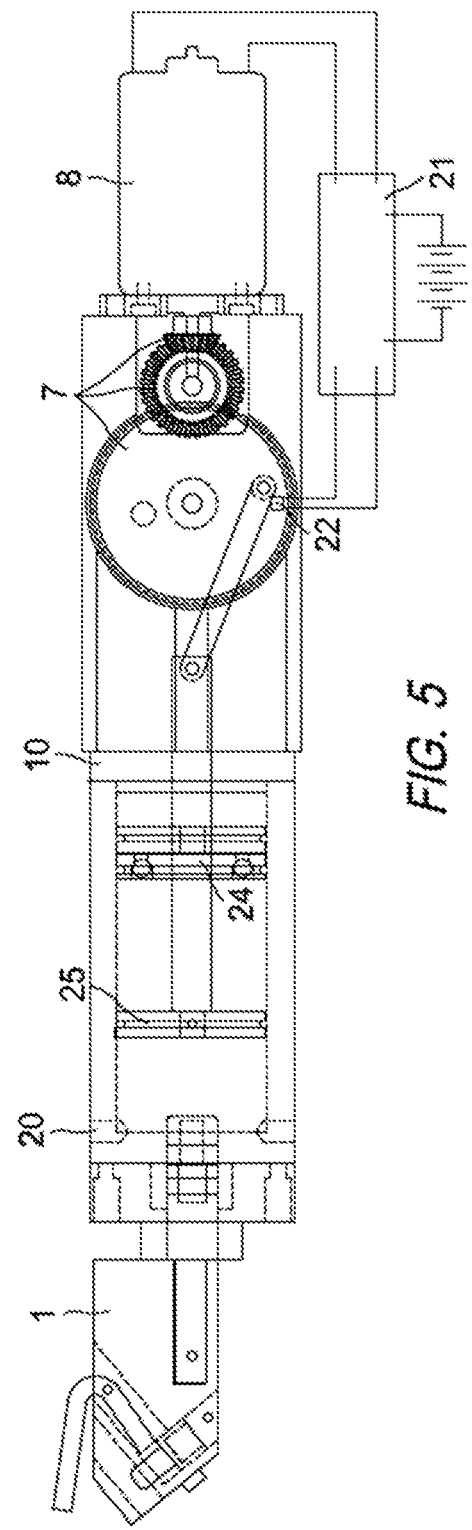
FIG. 5 shows a piston of the tool of FIG. 1 moving back towards a first position and resetting the striker.
Figure 6:
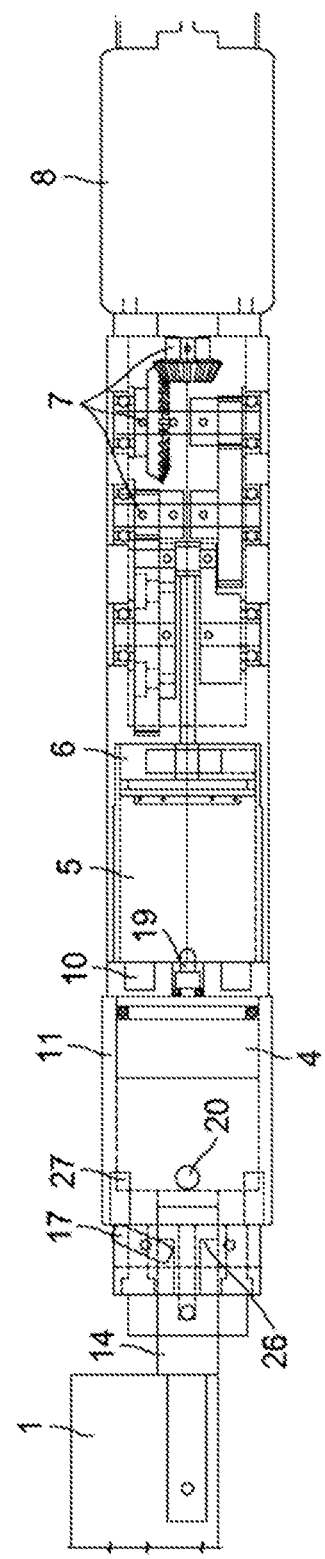
FIG. 6 shows a further exemplary embodiment of a tool in which a compression chamber is used to create an impacting force.
Figure 7:
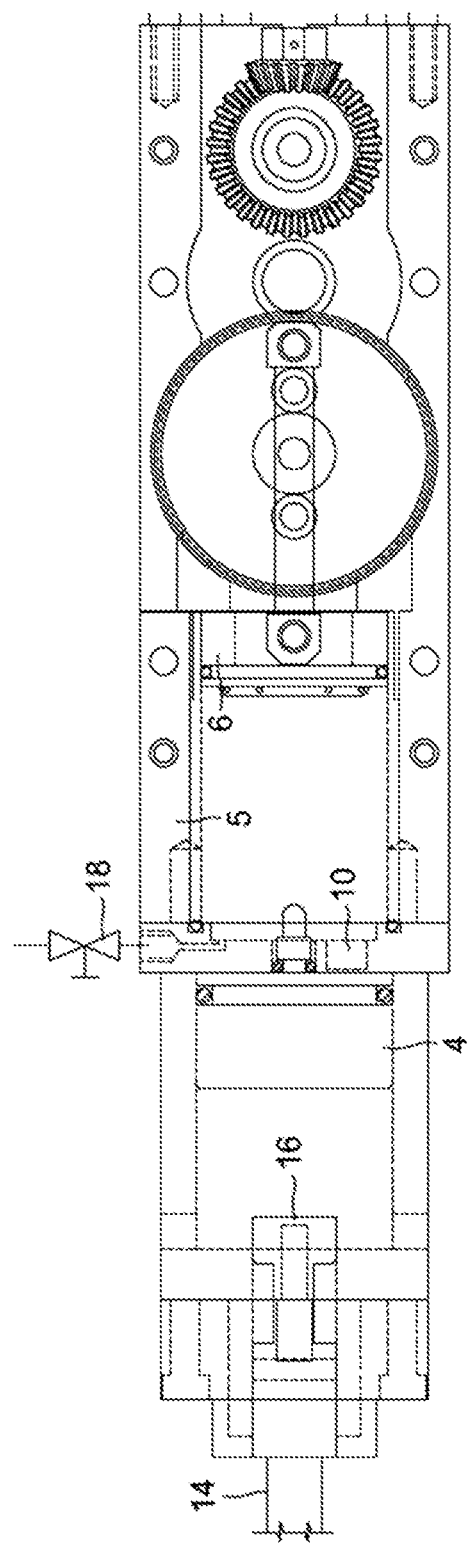
FIG. 7 shows an exemplary embodiment of a tool in which a valve is used to adjust the energy of the impact of the striker.
Figure 8:
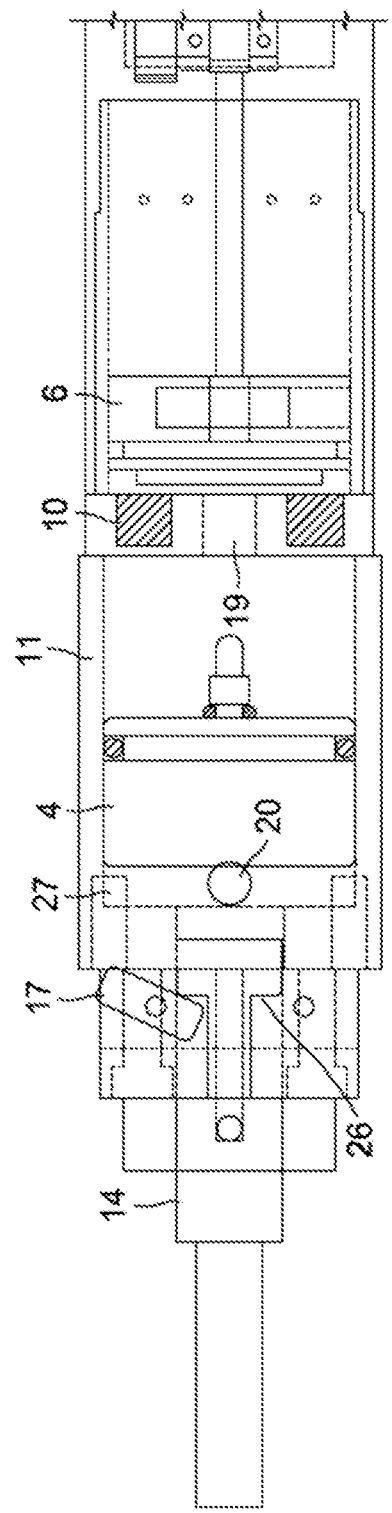
FIG. 8 shows an exemplary embodiment of a tool in which the striker imparts a surface imparting a rearward force on the anvil.
Figure 9:
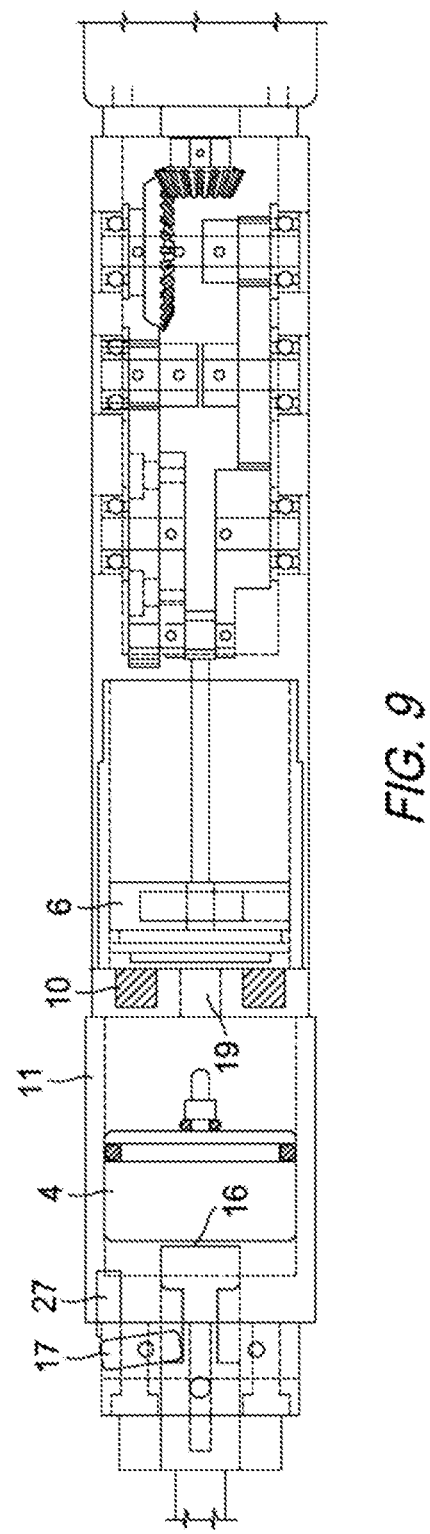
FIG. 9 shows an exemplary embodiment of a tool in which the striker imparts a forward acting force on the anvil.

In a further embodiment, the motor 8 of the tool causes the linear motion converter 12 to move the piston 24 until the piston 24 moves a sufficient distance such that the forward portion of the piston impacts a portion of the striker and overcomes the detent 10 that retains the striker in the rear position. Once the striker has been released from the detent 10, the vacuum in the vacuum chamber 23 exerts a force on the striker, which accelerates the striker, causing the striker to slide axially down a cavity internal to the tool housing and strike the anvil forward impact surface 16. In FIG. 3, the anvil forward impact surface 16 causes a forward movement of the anvil 14 and/or tool holder, and, in FIG. 4, the anvil retract impact surface 26 causes a rearward movement of the anvil 14 and/or tool holder. The resultant force is communicated through an end of the anvil 14 that is proximate to the anvil forward impact surface 16 and, optionally, through the adapter 1 to which a broach, chisel, or other end effector for seating or removing an implant or prosthesis may be attached.

In another exemplary embodiment, the impact force may be generated using a compressed air chamber 5 in conjunction with a piston 6 and striker 4, as shown generally in FIGS. 6 through 9. In this embodiment, the motor 8 of the tool causes the linear motion converter 12 to move the piston 6 until sufficient pressure is built within the compressed air chamber 5 that is disposed between the distal end of the piston 6 and the proximate end of the striker 4 to overcome a detent 10 that otherwise retains the striker 4 in a rearward position and or the inertia and frictional force that holds the striker 4 in that rearward position. Once this sufficient pressure is reached, an air passageway 19 is opened and the air pressure accelerates the striker 4, which striker 4 slides axially down a cavity and strikes the anvil 14. The air passageway 19 has a cross sectional area of preferably less than 50% of the cross sectional area of the striker 4 so as to reduce the amount of retaining force required from detent 10. The resultant force is communicated through the end of the anvil 14 that is proximate to the anvil forward impact surface 16 and, optionally, through the adapter 1 to which a broach, chisel, or other device for seating or removing an implant or prosthesis may be attached.

As the piston 6 continues through its stroke, it moves towards the rear direction, pulling a slight vacuum in compressed air chamber 5. This vacuum may be communicated through an air passageway 19 to the back side of the striker 4, creating a returning force on the striker 4, which returning force causes the striker 4 to move in a rear direction, i.e., a direction away from the point of impact of the striker 4 on the anvil forward impact surface 16. In the event that an adapter 1 is attached to the anvil 14, a force may be communicated through the adapter 1 to which the broach, chisel, or other end effector for seating or removing an implant or prosthesis is attached.

Figure 11:
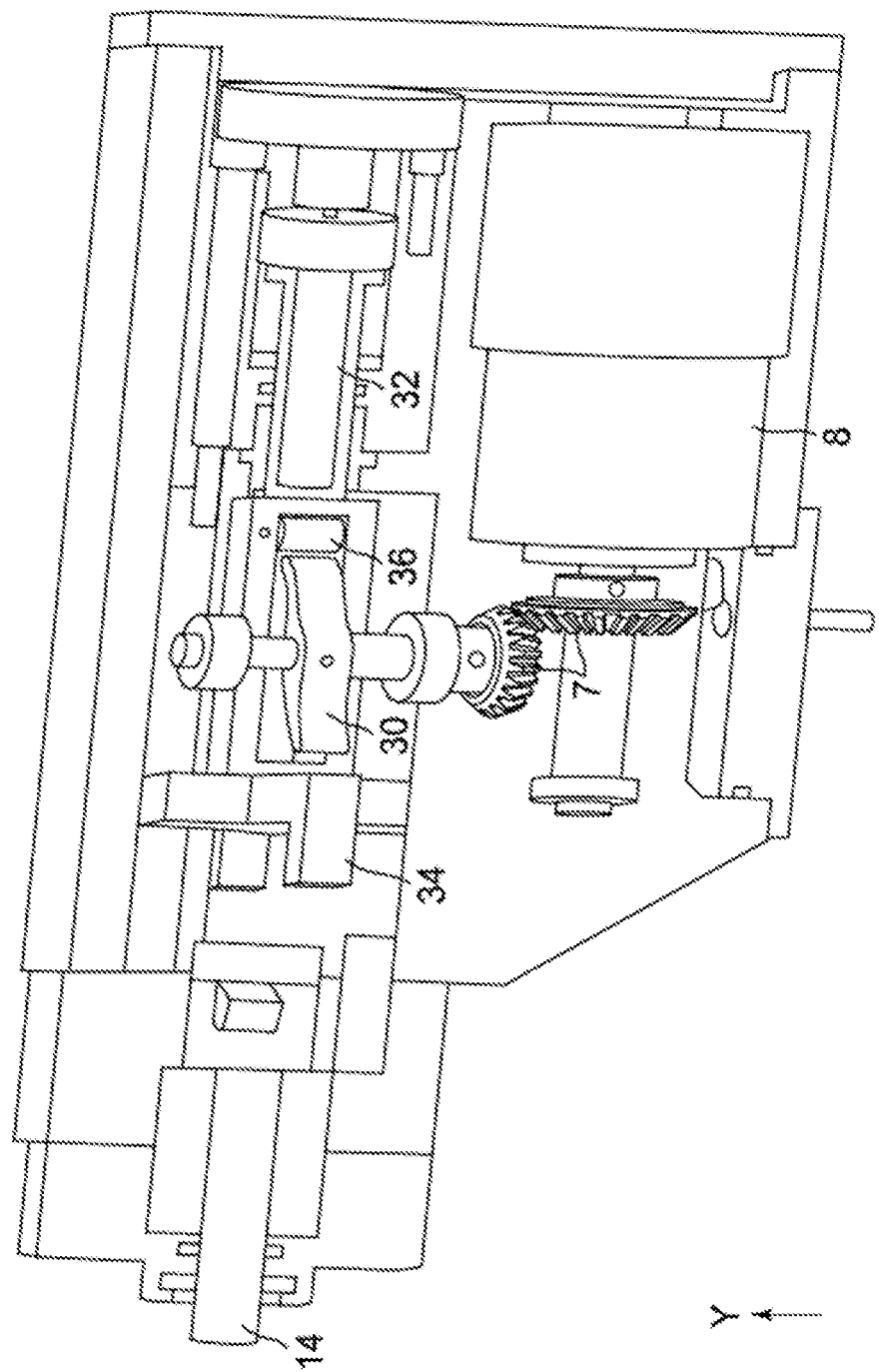
FIG. 11 shows a perspective view of an orthopedic impacting tool in accordance with a further embodiment of the present disclosure in which a gas spring assembly system is used for generating an impact force.

In another exemplary embodiment, the impact force may be generated using a gas spring assembly system, such as an air spring assembly system, as illustrated, for example, in FIG. 11. FIG. 11 shows a perspective view of an orthopedic impacting tool in accordance with an embodiment of the present disclosure in which a motor and gearbox 8 of the gas spring assembly system, in combination with a cam 30, actuates a gas spring piston 32 and/or a launched mass 34, in order to ultimately generate an impact force. The cam 30 is shown in tear drop shape, but the design contemplates that any shape may be used which provides a quick release of the gas spring. Alternative ways for actuating and quickly releasing the gas spring include, but are not limited to, using an interrupted rack and pinion or a climbing mechanism. The gas spring assembly system further includes, among other components, a roller follower 36, reducing gears 7 and an anvil 14. The gas spring piston 32 includes a gas chamber 40 which operates under pressure in a range of about 300 to 3000 psi, for example.

Figure 12:
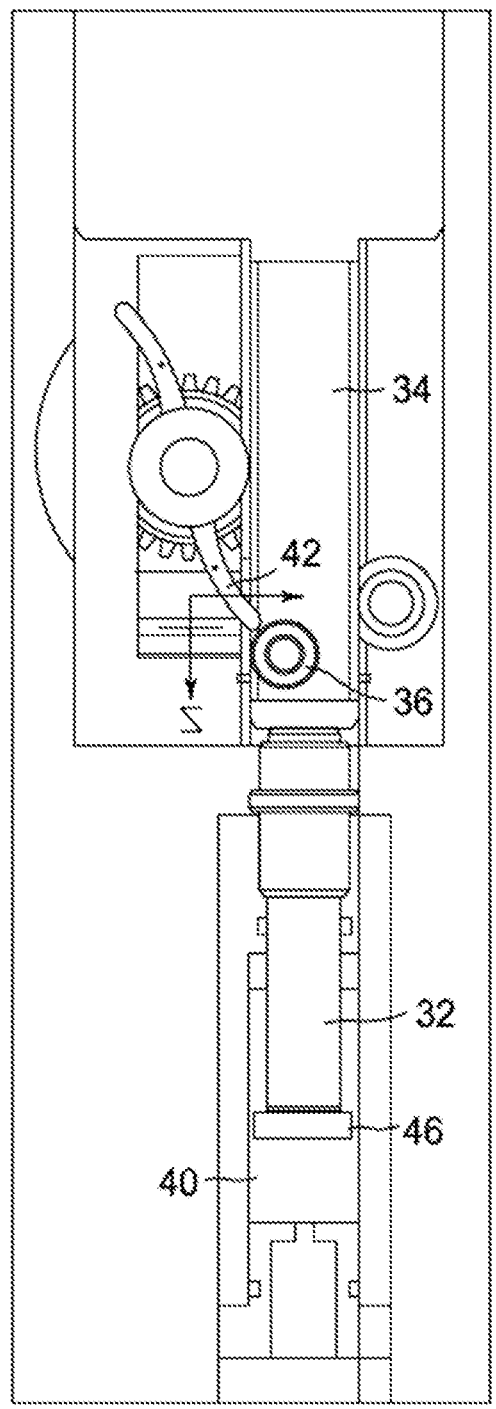
FIG. 12 shows a perspective view of the gas spring assembly system in which a cam is used for actuating a gas spring.

FIG. 12 is a perspective view of the gas spring assembly system in which the cam 30 used for actuating the gas spring piston 32 has the gas spring "cocked" in the operative position, ready for release. In the "cocking phase" the gas spring piston 32 in combination with the launched mass 34 contacts and is pushed by the roller follower 36, which is driven by the cam 30 in a first direction, as shown by arrow 42. As the cam 30 continues to rotate in the first direction (viewed as clockwise for tautological purposes), the gas spring piston 32 in combination with the launched mass 34 is released off of the cam 30. In particular, after a sufficient displacement of the gas spring piston 32 within the gas chamber 40, and after the cam 30 releases the gas spring piston 32 and/or the launched mass 34 combination, the gas spring piston 32 moves in a forward direction, i.e., a direction toward the point of impact, and, at the same time, accelerates the launched mass 34, which is in contact with the face of the gas spring piston 32. The launched mass 34 may be constructed from a suitable material such as steel or any other material having similar properties lending itself to repeated impacting.

Figure 13:
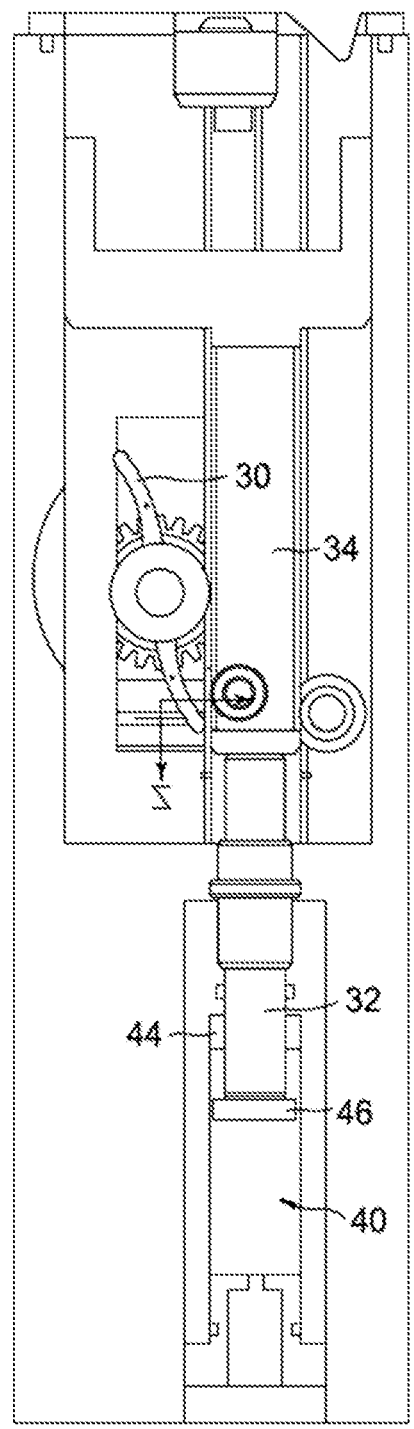
FIG. 13 shows an exemplary embodiment of the tool in which the cam of the gas spring assembly system has released the gas spring.
Figure 14:
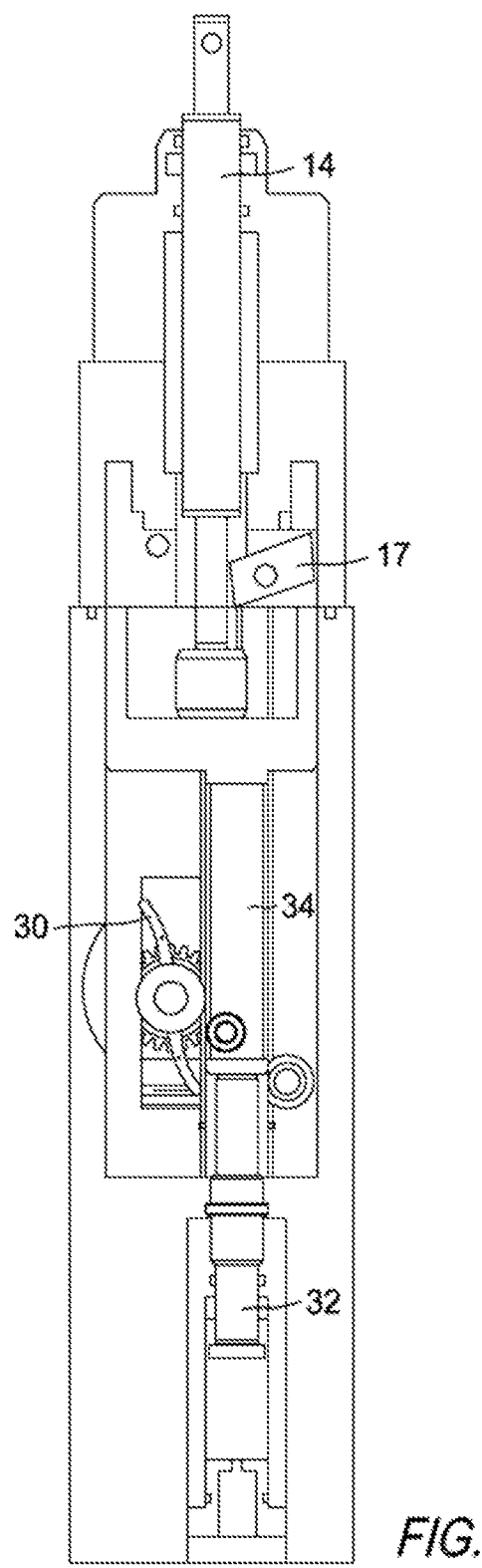
FIG. 14 shows an exemplary embodiment of the tool in which after the gas spring has been released, a launched mass is accelerated towards a point of impact in a forward direction.

FIGS. 13 and 14 show an exemplary embodiment of the orthopedic impacting tool in which the cam 30 of the gas spring assembly system has been rotated in the first direction 42 and the gas spring piston 32 has been released off of the cam 30. Upon release of the gas spring piston 32, the launched mass 34 is accelerated in the forward direction with the gas spring piston 32 until it comes into operative contact with the point of impact, the anvil 14 or another impact surface. As the gas spring piston 32 moves in the forward direction, a gas spring bumper 44 functions as a stopper to prevent a flange 46 of the gas spring piston 32 from impacting the cylinder of the gas spring piston 32. The bumper 44 absorbs the impact of the gas spring piston 32 as it comes to the end of the stroke and launches the mass 34. Such bumper 44 prevents damage to the gas spring piston 32 during repeated operation. During at least a portion of the impact, and preferably prior to the point of impact, the launched mass 34 separates from the face of the gas spring piston 32. The cam 30 then re-cocks the gas spring piston 32 for the next cycle, if a trigger is maintained.

As discussed above, there are at least two different impacting surfaces, a forward impact surface and a different surface for rearward impact. FIG. 14 shows the lever arm 17, which communicates a rearward force on the anvil 14, and specifically on a different surface for rearward impact. Such has the unexpected benefit of easily dislodging tools and instruments that have become stuck in a surgical cavity. With specific reference to FIGS. 6, 8 and 9, for example, when the orthopedic impacting tool is being pulled away from the cavity of a bone of the patient, for example, the striker 4 will not impact the anvil 14, but may instead impact an alternate surface and thereby communicate a rearward force on the anvil 14. This impact surface is shown in an exemplary embodiment as actuation pin 27. Actuation pin 27 communicates a force to lever arm 17, which communicates a rearward force on the anvil 14, and specifically on the anvil retract impact surface 26.

The ratio of the gas spring piston 32 mass to the total moving mass, i.e., the gas spring piston 32 in combination with the launched mass 34, is less than about 50%, which facilitates a more efficient energy transfer to the launched mass 34 for imparting an effective impact on the impact surface. Advantageously, the gas spring assembly system does not need or use a detent or a magnet for generating the higher energy impact. Further, the compression ratio of the gas spring is less than 50%, which reduces thermal heat generated during the compression of the gas. Accordingly, the gas spring assembly system is more compact, efficient, weighs less and has less total and moving parts as compared to the earlier described impact generating systems.

The tool may further facilitate controlled continuous impacting, which impacting is dependent on a position of a start switch (which start switch may be operatively coupled to the power source or motor, for example). For such continuous impacting, after the start switch is activated, and depending on the position of the start switch, the tool may go through complete cycles at a rate proportional to the position of the start switch, for example. Thus, with either single impact or continuous impacting operational modes, the creation or shaping of the surgical area is easily controlled by the surgeon.

A sensor 22 coupled operatively to the controller 21 may be provided to assist in regulating a preferred cyclic operation of the linear motion converter 12. For example, the sensor 22 may communicate at least one position to the controller 21, allowing the linear motion converter 12 to stop at or near a position in which at least about 75% of a full power stroke is available for the next cycle. This position is referred to as a rest position. This has been found to be advantageous over existing tools in that it allows the user to ensure that the tool impacts with the same amount of energy per cycle. Without this level of control, the repeatability of single cycle impacting is limited, reducing the confidence the surgeon has in the tool.

The tool is further capable of tuning the amount of impact energy per cycle by way of, for example, an energy control element 18. By controlling the impact energy the tool can avoid damage caused by uncontrolled impacts or impacts of excessive energy. For example, a surgeon may reduce the impact setting in the case of an elderly patent with osteoporosis, or may increase the impact setting for more resilient or intact athletic bone structures.

In an embodiment, the energy control element 18 preferably comprises a selectable release setting on the detent 10 that holds the striker 25. It will be apparent that the striker 25 will impact the anvil 14 with greater energy in the case where the pressure needed to dislodge the striker 25 from the detent 10 is increased. In another embodiment, the detent 10 may comprise an electrically controlled element. The electrically controlled element can be released at different points in the cycle, thus limiting the size of the vacuum chamber 23, which is acting on the striker 25. In an embodiment, the electrically controlled element is an electromagnet.

In another embodiment, the vacuum chamber 23 or compressed air chamber 5 may include an energy control element 18, which takes the form of an adjustable leak, such as an adjustable valve. The leakage reduces the amount of energy accelerating the striker 4 or 25, thus reducing the impact energy on the anvil 14. In the case of the adjustable leak, adjusting the leak to maximum may give the lowest impact energy from the striker 4 or 25, and adjusting to shut the leak off (zero leak) may give the highest impact energy from the striker 4 or 25.

Figure 10:
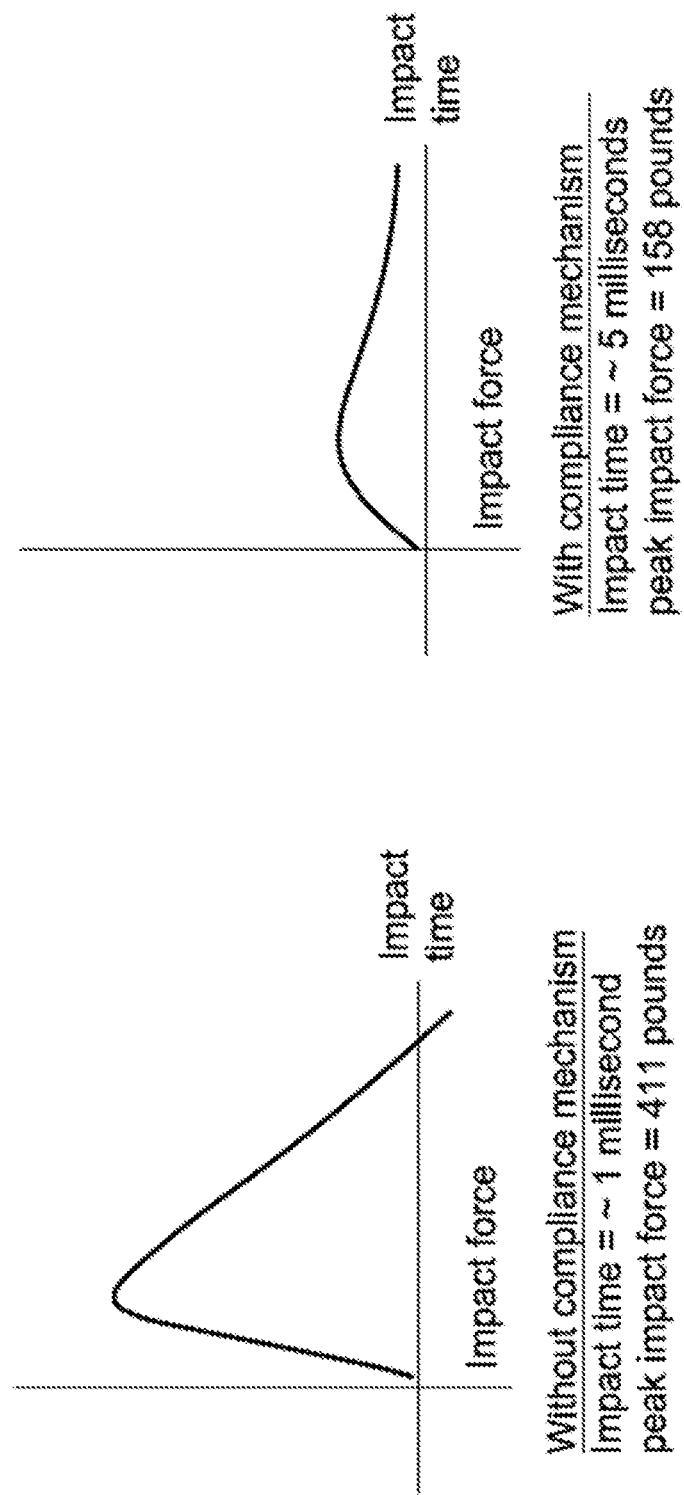
FIG. 10A is a chart showing a force vs. time for a sharp impact.
FIG. 10B is a chart showing a force vs. time curve for a modified impact using a compliance mechanism in accordance with an exemplary embodiment of the present disclosure.

The tool may further comprise a compliance element inserted between the striker 4 or 25 and the surgical end effector, which purpose is to spread the impact force out over a longer time period, thus achieving the same total energy per impact, but at a reduced force. This can be seen clearly as a result of two load cell tests on the instrument as shown in FIGS. 10A and 10B. This type of compliance element can limit the peak force during impact to preclude such peaks from causing fractures in the patient's bone. In a further embodiment, this compliance element may be adjustable and in a still further embodiment the compliance element may be inserted between striker 4 or 25 and the anvil 14 or surgical tool. In this manner and otherwise, the tool facilitates consistent axial broaching and implant seating. Preferably, the compliance Element increases the time of impact from the striker to at least 4 milliseconds and preferable 10 milliseconds. This contrasts to impacting in which a very high force is generated due to the comparatively high strengths of the striker 4 or 25 and the anvil 14 (both steel, for example). Preferably, the compliance Element comprises a resilient material such as urethane, rubber or other elastic material that recovers well from impact and imparts minimal damping on the total energy.

In a further embodiment, the adapter 1 may comprise a linkage arrangement or other adjustment mechanisms known in the art such that the position of the broach, chisel or other end effector can be modified without requiring the surgeon to rotate the tool. In an embodiment, the adapter 1 may receive a broach for anterior or posterior joint replacement through either an offset mechanism or by a rotational or pivotal coupling between the tool and the patient. The adapter 1 may thereby maintain the broach or surgical end effector in an orientation that is parallel or co-linear to the body of the tool and the striker 25. The adapter 1 may also comprise clamps, a vice, or any other fastener that may securely hold the broach, chisel, or other end effector during operation of the tool.

In use, a surgeon firmly holds the tool by the handle grip or grips and utilizes light emitted by the LED to illuminate a work area and accurately position a broach, chisel or other end effector that has been attached to the tool on a desired location on the prosthesis or implant. The reciprocating movement imparted by the tool upon the broach, chisel or other end effector allows for shaping a cavity and for seating or removal of a prosthesis.

The tool disclosed herein provides various advantages over the prior art. It facilitates controlled impacting at a surgical site, which minimizes unnecessary damage to a patient's body and which allows precise shaping of an implant or prosthesis seat. The tool also allows the surgeon to modulate the direction, force and frequency of impacts, which improves the surgeon's ability to manipulate the tool. The force and compliance control adjustments of the impact settings allow a surgeon to set the force of impact according to a particular bone type or other profile of a patient. The improved efficiency and reduced linear motion converter loads allow use of smaller batteries and lower cost components. The tool thereby enables proper seating or removal of the prosthesis or implant into or out of an implant cavity.

The foregoing descriptions of specific embodiments of the present disclosure have been presented for purposes of illustration and description. They are not intended to be exhaustive or to limit the present disclosure to the precise forms disclosed, and obviously many modifications and variations are possible in light of the above teaching. The exemplary embodiment was chosen and described in order to best explain the principles of the present disclosure and its practical application, to thereby enable others skilled in the art to best utilize the disclosure and various embodiments with various modifications as are suited to the particular use contemplated.

What is claimed is:

1. A surgical impactor for striking an object with a repeatable, controlled contacting force to impel the operation of a surgical implement in opposing directions, the impactor comprising:
    a drive mechanism with a gas spring assembly;
    a control circuit configured to control storage and release of energy output from the drive mechanism to an energy storage mechanism to produce the repeatable, controlled contacting force;
    an adapter configured to receive a surgical implement to interface the object; and
    a moving body operable to contact at least two distinct impact surfaces based upon the repeatable, controllable contacting force delivered thereto to provide the repeatable controlled contacting force to the adapter, the provision of the repeatable, controllable contacting force to a first impact surface being configured to impel the adapter in a first direction, the provision of the repeatable controllable contacting force to a second impact surface being configured to impel the adapter in a direction opposite the first direction;
    wherein the gas spring assembly includes a gas spring, a gas spring piston, a cam, a motor, and a gearbox; and
    wherein the cam is configured to displace the gas spring piston.

2. The impactor of claim 1, wherein selection of the at least two impact surfaces is based upon a user bias force applied to the impactor;
    the user bias force in a direction of the object is configured to cause the moving body to contact the first impact surface; and
    the user bias force in a direction away from the object is configured to cause the moving body to contact the second impact surface.

3. The impactor of claim 1, wherein a ratio of a gas piston mass to a total moving mass of the gas spring piston and the moving body is less than 50%.

4. The impactor of claim 1, wherein a compression ratio of the gas spring is less than 50%.

5. The impactor of claim 1, wherein the gas spring piston includes a gas chamber configured to operate under a pressure in a range of 300 to 3000 psi.

6. The impactor of claim 1, further comprising:
    an energy adjustment mechanism configured to adjust impact energy the moving body delivers to the adapter in accordance with a patient profile.

7. The impactor of claim 1, wherein the moving body is operably linked to the adapter by an anvil.

8. The impactor of claim 7, wherein the adapter is configured to be impelled in the direction opposite the first direction by a lever arm configured to apply a rearward force on the anvil.

9. The impactor of claim 1, wherein the cam is configured to engage the gas spring piston prior to the moving body contacting the at least two distinct impact surfaces, and the cam is configured to release the gas spring piston from the cam to impel the moving body to contact the at least two distinct impact surfaces.

10. The impactor of claim 1, wherein the moving body is attached to a face of the gas spring piston prior to contacting the at least two distinct impact surfaces; and the moving body is configured to separate from the face of the gas spring piston during at least a portion of the contact with the at least two distinct impact surfaces.

11. A surgical impactor for striking an object with a repeatable, controlled contacting force to impel the operation of a surgical implement in opposing directions, the impactor comprising:

means for driving the impactor with a gas spring assembly, the gas spring assembly including a gas spring piston;

a control circuit configured to control storage and release of energy, of the means for driving, to an energy storage device to produce the repeatable, controlled contacting force;

an implement mount configured to receive a surgical implement; and a moving body operable to contact at least two distinct impact surfaces based upon the repeatable, controllable contacting force delivered thereto to provide the repeatable controlled contacting force to the implement mount, the provision of the repeatable, controllable contacting force to a first impact surface being configured to impel the implement mount in a first direction, the provision of the repeatable controllable contacting force to a second impact surface being configured to impel the implement mount in a direction opposite the first direction.

12. A surgical impactor, comprising:

an adapter configured to releasably connect to a surgical end effector;

a striker;

a cam;

a motor configured to be actuated and thereby cause movement of the cam, the movement of the cam being configured to cause the striker to move and communicate a force to the adapter, thereby causing the adapter to communicate a force to the surgical end effector releasably connected to the adapter; and a mass releasably coupled to the striker, wherein the movement of the striker is configured to cause movement of the mass such that the mass impacts an impact surface to communicate the force to the adapter.

13. The impactor of claim 12, further comprising a piston, wherein:

the movement of the cam causes the piston to move; and the movement of the piston causes the movement of the striker.

14. The impactor of claim 13, further comprising a gas chamber, wherein the movement of the piston includes movement of the piston within the gas chamber.

15. The impactor of claim 13, wherein the movement of the cam causes the piston to be released from the cam and move relative to the cam.

16. The impactor of claim 12, wherein the mass is in contact with a face of the striker prior to the movement of the striker, and the movement of the mass causes the mass to separate from the face of the striker.

17. The impactor of claim 12, wherein the movement of the cam is rotational movement, and the movement of the striker is longitudinal translational movement.

18. The impactor of claim 12, further comprising a controller configured to control cyclic movement of the striker such that the striker repeatedly moves and repeatedly communicates the force to the adapter.

19. The impactor of claim 12, further comprising an anvil, wherein the force is communicated to the adapter via an anvil.

* * * * *